United States Patent
Szasz et al.

(10) Patent No.: US 9,675,813 B2
(45) Date of Patent: Jun. 13, 2017

(54) PORTABLE RADIOFREQUENCY HYPERTHERMIA DEVICE WITH FLEXIBLE TREATMENT ELECTRODE FOR ELECTRIC FIELD CAPACITIVE COUPLED ENERGY TRANSFER

(75) Inventors: Andras Szasz, Páty (HU); Oliver Szasz, Páty (HU); Nora Iluri, Weston, MA (US)

(73) Assignee: Oncotherm Kft., Páty (HU)

( * ) Notice: Subject to any disclaimer, the term of this patent is extended or adjusted under 35 U.S.C. 154(b) by 653 days.

(21) Appl. No.: 13/058,487

(22) PCT Filed: Aug. 14, 2009

(86) PCT No.: PCT/EP2009/006052
§ 371 (c)(1),
(2), (4) Date: May 11, 2011

(87) PCT Pub. No.: WO2010/018001
PCT Pub. Date: Feb. 18, 2010

(65) Prior Publication Data
US 2011/0208182 A1    Aug. 25, 2011

(30) Foreign Application Priority Data
Aug. 14, 2008  (EP) .................................. 08075703

(51) Int. Cl.
*A61N 1/40*   (2006.01)
(52) U.S. Cl.
CPC .................... *A61N 1/403* (2013.01)

(58) Field of Classification Search
USPC ..... 607/98–102, 115, 152, 154–156; 604/20; 606/27, 32–34, 41; 128/898
See application file for complete search history.

(56) References Cited

U.S. PATENT DOCUMENTS

| 4,067,342 | A | * | 1/1978 | Burton ................. 607/152 |
| 4,121,592 | A | * | 10/1978 | Whalley ............... 607/98 |
| 4,140,130 | A | * | 2/1979 | Storm, III ............ 607/154 |
| 4,186,729 | A | * | 2/1980 | Harrison .............. 600/10 |
| 4,419,091 | A | * | 12/1983 | Behl et al. ........... 604/20 |

(Continued)

FOREIGN PATENT DOCUMENTS

EP    1916013    4/2008

OTHER PUBLICATIONS

Wust "Thermoregulation in humans. Experiences from thermotherapy" Stuttgart, Nov. 21-23, 2005.

(Continued)

*Primary Examiner* — Joseph Stoklosa
*Assistant Examiner* — Adam Avigan
(74) *Attorney, Agent, or Firm* — Meyertons, Hood, Kivlin, Kowert & Goetzel, P.C.; Eric B. Meyertons (57) ABSTRACT

The present disclosure relates to a portable radiofrequency (RF) hyperthermia device having flexible applicator treatment electrodes for electric field capacitive coupled energy transfer, the device being useful for increasing the delivery of a systemically delivered drug at a localized target site. The portable RF device is suitable for use by a patient in their own home and the flexible applicator is a flexible, porous, light and easy to manipulate treatment electrode. The inventive device requires no specialist operator to ensure correct usage.

8 Claims, 3 Drawing Sheets

(56) References Cited

U.S. PATENT DOCUMENTS

| | | |
|---|---|---|
| 6,219,577 B1 | 4/2001 | Brown et al. |
| 6,287,297 B1 | 9/2001 | Woodruff et al. |
| 6,330,479 B1 | 12/2001 | Stauffer |
| 6,662,044 B2 | 12/2003 | Crawford et al. |
| 7,767,936 B2 | 8/2010 | Furguson |
| 2003/0208152 A1* | 11/2003 | Avrahami ............ A61N 1/325 604/20 |
| 2004/0254618 A1 | 12/2004 | Schroeppel et al. |
| 2006/0293730 A1* | 12/2006 | Rubinsky et al. ............. 607/98 |
| 2007/0255271 A1* | 11/2007 | Dabney et al. ................ 606/39 |
| 2008/0288025 A1* | 11/2008 | Peterson ....................... 607/60 |

OTHER PUBLICATIONS

Wust "Subtle thermal effects of RF-Fields in vitro and in vivo" Stuttgart, Nov. 21-23, 2005.

* cited by examiner

Treated tumor 1.16 mL  
0.70 MBq (Increased uptake by 46%)

Control tumor: 1.15 mL  
0.38 MBq

PORTABLE RADIOFREQUENCY HYPERTHERMIA DEVICE WITH FLEXIBLE TREATMENT ELECTRODE FOR ELECTRIC FIELD CAPACITIVE COUPLED ENERGY TRANSFER

BACKGROUND OF THE INVENTION

1. Field of the Invention

The present invention relates to a portable radiofrequency (RF) hyperthermia device having flexible applicator treatment electrodes for electric field capacitive coupled energy transfer, the device being useful for increasing the delivery of a systemically delivered drug at a localised target site. The portable RF device is suitable for use by a patient in their own home and the flexible applicator is a flexible, porous, light and easy to manipulate treatment electrode. The inventive device requires no specialist operator to ensure correct usage.

2. Description of the Relevant Art

Heating is widely applied in a many areas of medicine and also used for cosmetic treatments. For example radiofrequency/microwave hyperthermia devices can be used to force energy absorption in tissue to cause damage to unwanted structures and/or increase the temperature of a targeted area above the normal body temperature. One use of hyperthermia devices is the treatment of cancer. Another use for hyperthermia devices is to increase temperature and blood circulation for cosmetic (fat-burning, lipid-distortion, shape-correction, etc), dermatological and pain relief treatments.

A usual therapy for many diseases for curative and/or palliative purposes is the administration of a drug. A drug can be administered by a number of possible routes, for example, orally and/or intravenously and/or injected into muscles or arteries. These modes of drug delivery result in systemic exposure to the drug. However, the disease is often mainly localized to a specific area, such as a particular organ (liver, lung, kidney, prostate, breast, brain, spleen, stomach, oesophagus, colon, pancreas, etc.). Therefore the maximum exposure to the drug is required only, or mostly, at a localised target site. A common problem of drugs that are required at a local target but are systemically delivered is their systemic actions. The negative consequences are not trivial:

unwanted side effects occur often requiring further treatment to ameliorate the side effects, the administration of the drug is non-selective and a lower amount of the drug reaches the target site than intended, a higher dose of drug must be administered than is required at the target site to ensure delivery of a sufficient drug concentration at the target site.

U.S. Pat. No. 6,330,479 is a state of the art document disclosing a hyperthermia device which uses microwaves. The basic idea of the device described in U.S. Pat. No. 6,330,479 is far from the present disclosure. U.S. Pat. No. 6,330,479 discloses a portable belt or garment for inducing hyperthermia. It is a surface heating, when the microwave has a role to keep the liquid warm (keep on definite temperature) and so heat up the skin where the belt/garment is fixed. The similarity that it fits well to different body contours is very formal, because the heating mechanism does not fit at all. The applicator (belt/garment) in U.S. Pat. No. 6,330,479 has a contact heating making the blood-perfusion high in the surface area, and remaining ineffective in the deep target. The heat is not generated in depths and consequently the effect of the present disclosure isn't realized. If (by long-time application) the heating could reach deeper volumes it does not promote selective drug delivery, because of the above. In principle, not targeted layers have a higher temperature so they are targeted by the medicaments of the ionizing radiation much more than the selected tissue itself. The contact hot-spots (and their elimination by distances) is also far from the present disclosure and solution. The present deep heating does not heat up the surface. At the contrary, it is taken care on its proper cooling by a porous structure or even by extra air or fluid cooling. The extra cooling process in U.S. Pat. No. 6,330,479 is a large, complex and complicated solution. The metalized porous textile or other suitable materials of the present disclosure such as conductively coated flexible carrier, coated flexible material, conductive metallic net or a conductive metallic network can be used for manufacturing of at least one conductive metal electrode material. Such metallic nets or metallic networks do preferably not comprise any backbone such as a polymeric network structure. The metallic net or network is preferably a woven structure of metallic fibers having very similar properties as the coated flexible material such as a coated textile. Such metalized porous textile or other suitable materials automatically solve the heating problem without additional technical efforts. Temperature measurement isn't necessary either in the present disclosure (but as an additional option it could be done on the surface). The temperature control is simply the patient's sensing. It isn't intended to heat up the surface higher than tolerable. For the wanted physiological effect not more than 42° C. are needed locally. This is requested for the targeted volume. Higher temperature could cause an opposite effect; it could block the blood-perfusion in the capillaries, mainly in solid tumors. The surface heating (according to U.S. Pat. No. 6,330,479) faces the problem of a temperature gradient, which requires the comparatively highest temperature at the surface to penetrate deeper. The disclosed portable RF hyperthermia device does the opposite. The surface could be kept on body temperature and at the same time the targeted volume could be heated up by penetration of the RF-current. The device constructed according to U.S. Pat. No. 6,330,479 appears rather complicated to handle as well as uncomfortable to wear for the patient and delimits considerably his/her mobility. The aim of improved drug availability in the heated tissue is not addressed at all in U.S. Pat. No. 6,330,479 and it cannot be achieved because the increased blood perfusion is limited to the surface area.

U.S. Pat. No. 6,330,469 discloses a completely a different apparatus and a completely different idea of application than the present disclosure. It does not provide the advantages of selective drug targeting (except at the surface area), it compromises the patient's mobility and it can not heat in deeper layers. The present disclosure does not require a cooling system and an easy handling will provide a positive feedback in the long run.

WO 00/51513 A is another state-of-the-art document disclosing an invasive energy delivering system, dedicated to a special need of vascularization. It is not drug- or radio-targeting and it does not target capillaries. This is a highly specialized device in heart physiology (cardiology). In contrast, the present disclosure is a non-invasive heat-delivery device for any body part, it is promoting the revascularization of capillaries, it can be combined with systemically administered drugs (even in oral, inhalatory, topical, parenteral, injection or other systemic drug delivery). The drugs can be effectively reoriented and redistributed to the desired (targeted) tissue especially due to increased blood-perfusion. WO 00/51513 A clearly reveals an invasive method. This device is only suitable for the use in hospital. The patient is under full anaesthesia or at least highly sedated and immobilized. The present disclosure allows the patient a comparatively wide range of moving around freely, no further medication (palliative or other safety medication) is necessary for its application. The device from WO 00/51513 A uses water cooling channels inside the catheter for keeping the surface temperature in a safe range. In this aspect WO 00/51513 A uses the same solution as in U.S. Pat. No. 6,330,469: It has conductive heat-diffusion, it provides the highest temperature at the outermost surface of the application area and the heat flows according to the temperature gradient. Both U.S. Pat. No. 6,330,469 and WO 00/51513 A are typical thermal conductivity systems showing all the disadvantages of this approach. U.S. Pat. No. 6,330,469 and WO 00/51513 A are much more similar to each other than to the present disclosure.

SUMMARY OF THE INVENTION

At present, most pharmaceutical products are administered systemically or topically, for example by:
  oral administration,
  venal infusion (i.v.),
  muscular injection,
  arterial infusion,
  rectal suppository,
  topical application (including pressure or osmotic- and/or iontophoretic pharma-products),
  heat baths with herbs, salts or other drugs, and
  inhalations, aroma-therapies, etc.

As a result the drug is usually delivered to the desired target site by the blood stream. Therefore increasing the blood flow to the local target site or increasing the blood perfusion inside the local target site will increase the delivery of a systemically applied drug to the local target site.

The present disclosure provides a device and method for local deep heating to increase the blood flow and/or blood perfusion in a local area.

Local temperature actively modifies blood-flow and blood perfusion. In humans the organ systems have the potential to increase the perfusion 5-10 fold as a self-protective mechanism against harmful temperature elevation (Wust P: Thermoregulation in humans, Experiences from thermotherapy, Workshop "Subtle thermal effects of RF-fields in vitro and in vivo", Stuttgart, 21-23, November 2005). The increase of local blood flow and blood perfusion by local heating is a simple dynamic selection method, instead of a homogeneous distribution throughout the body.

The metabolic rate also depends exponentially on the temperature. A seven degree increase in temperature doubles the metabolic rate. However, the metabolic rate is also connected to the blood flow. The blood flow increases in order to carry away excess heat generated through increased metabolism. On the other hand, decreased blood flow can cause a lack of oxygen, thus slowing the metabolism. This effect acts as a positive feedback mechanism and significantly modifies the heat distribution. Since the inventive device is able to increase blood-flow, oxygen delivery as well as metabolism is increased.

Considering the specific absorption rate of the energy (SAR) with application of simple equilibrium thermodynamics using the usual notations: Q—heat-energy [J], SAR—specific absorption rate [J/kg], m—mass [kg], c—specific heat [J/kg/K] (for dilute aqueous solutions like electrolytes in a living system it is supposed to amount to ~4200 J/kg/K), t—time [s], T—temperature [K], P—applied power [W], Δ—denotes the change of the value respectively the temperature gain:

$$\frac{Q}{mc} = \frac{P \cdot \Delta t}{mc} = \frac{SAR \cdot \Delta t}{c} = \frac{SAR \cdot \Delta t}{4200} = \Delta T[^\circ C.]$$

The blood-flow is on average BF ~3.5 kW/m3/K=3.5 W/liter/K, ~0.2 liter/s/kg is the average blood-perfusion, which decreases a possible temperature gain, together with the increase in metabolic heat. However, not a temperature gain is aimed at, but a higher blood-flow to support a chemotherapeutic and/or radiotherapeutic treatment.

The heat effect on blood flow has been well studied in the field of oncology. An effective vascular response to heating is observed. However, above a tumor specific temperature threshold a differentiation between the malignant-tumor and normal/benign tissues occurs resulting in suppressed and increased blood perfusion, respectively. The large difference between the absolute blood flow in tumors and in healthy tissue has been long recognized, as well as the relative change of the blood-flow due to temperature. Relative blood-flow changes in healthy tissue and in tumor tissues are corresponding below the specific temperature threshold, starting at 38° C. The maximal temperature threshold value in literature is 42.5° C. This limit corresponds well with the assumed cellular phase transition of tumor cells observed around 42.5° C. Above this limit the change in blood flow suddenly splits, with the blood-flow further increasing in healthy tissue, while being down-regulated in tumor tissue.

In one embodiment, an apparatus and method are provided for increasing the delivery of a systemically delivered drug at a localized target site that is simple to use and suitable for home use by a patient.

In one embodiment, a portable (preferably fixed) radiofrequency (RF) hyperthermia device has flexible applicator treatment electrodes for electric field capacitive coupled energy transfer, the device being useful for increasing blood perfusion and/or blood flow. Further advantageous features, aspects and details of the invention are evident from the dependent claims, the description, and the examples of the present application.

BRIEF DESCRIPTION OF THE DRAWINGS

Advantages of the present invention will become apparent to those skilled in the art with the benefit of the following detailed description of embodiments and upon reference to the accompanying drawings in which.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

The present disclosure is directed to a portable hyperthermia device and a method for increasing the blood flow in a localized target area, thus increasing the delivery of a systemically delivered drug to a local target site especially for cancer treatment.

The increased blood volume to a local target site results in an increase in drug concentration at the target site corresponding to the increase in blood volume. In addition the increased drug concentration at the desired local target site results in a simultaneous slight decrease in the drug concentration at non-target sites, thus in tendency diminishing unwanted side effects outside the target site.

The temperature controlled blood flow enhancement provides several further advantages:

1. Increasing the arterial circulation and vasodilation, thus giving rise to increased oxygenation and a decreased acidity of the tissue.
2. The pharmacological effectiveness of the delivered drug increase exponentially with temperature (Boltzmann law) so the efficacy of the drug is increased at the target site.
3. Increasing the permeability of the cellular membrane, thus allowing better transfer of metabolites through the membrane and drug metabolism being increased at the target site.
4. This increased blood flow also provides an increase in the $pO_2$ (oxygen partial pressure) at the local target site which supports drug metabolism.
5. The normal metabolic rate also increases, thus producing extra heat and allowing for a higher selectivity of the local target site.
6. Increasing the venous drainage resulting in greater re-absorption of catabolites and decreasing edema in areas with inflammatory processes.
7. Speeding up of cicatrization of wounds.
8. Stimulating the immune system and decreasing free radicals. The immune stimulation is in general connected to elevated body temperature (fever).

The enhanced blood perfusion provided by the device and method of the embodiments disclosed herein also support the effect of radiotherapy due to increased oxygenation at the local target site.

The increased blood flow provided by the device and method of the embodiments disclosed herein is useful for therapy in the areas of traumatology and rehabilitation, rheumatology, sports medicine, neurosurgery and neurology, dermatology and pain management.

The local target site can be selected from tumor tissues and muscle tissue, or organs, such as liver, lung, heart, kidney, spleen, brain, ovary, uterus, prostate, pancreas, larynx, the gastrointestinal tract and the gynaecological tract To achieve an increased blood flow and/or blood perfusion the temperature of a local target site is raised by the use of a portable radiofrequency (RF) device having flexible applicator treatment electrodes for electric field capacitive coupled energy transfer to create an RF current flow through the body, resulting in an increase in temperature of the local target site due to the absorbed Joule heat. The portable radiofrequency device preferably works with a fixed radiofrequency, built in by the manufacturer to avoid interference with legally reserved frequency bands.

Thus the embodiments disclosed herein relate to a portable radiofrequency hyperthermia device having a flexible applicator treatment electrode for electric field capacitive coupled energy transfer. The inventive device is useful for increasing the delivery of a systemically delivered drug to and at a local target site, and/or supports the radiotherapy efficacy in the local target site by increasing tissue oxygenization, wherein the flexible applicator treatment electrodes comprise at least one conductive metal electrode material in form of a coating or a metallic net, wherein at least one conductive metal electrode material layer is coated onto the surface of a flexible, elastic or stretchable carrier, and wherein the coated flexible, elastic or stretchable carrier is porous; or wherein the at least one conductive metal electrode material constructs a flexible, elastic or stretchable carrier in form of a metallic net, and wherein the flexible, elastic or stretchable carrier is porous.

The term "target site" or "localized target site" or "local target site" refers to a tissue, preferably the diseased tissue, which requires treatment, preferably heat treatment and/or which requires an increased amount or concentration of a drug and/or which requires oxygenization.

Preferably the portable device is a resonant RF amplifier (E-class) having a fixed and definite frequency over 4 kHz and below 15 MHz. The claimed device does not require auto-matching or other fine tuning solutions, and the reflected power can be tolerated by the generator which is designed to tolerate a high overload. The applied power ranges from 10 to 200 W. Preferably the applied power is 40 W, which is suitable for most applications. The reflected power is a common problem in all radiofrequency applications. Herein the load and the transmitter are not matched and in consequence a reactive power appears. It is the same as in the cosinus-phi problem [phase shift] at the power lines. Thus the reflected power is the reactive part of the fully applied power.

Optionally (and in sensitive skin areas preferably), a power impulse regime is applied. This means the power is active in one time period and out of power in the next time period. The ratio of the pulses determines the average useful power during a longer time period. The intervals during which no power is provided should be set longer in sensitive cases so that the surface area could be cooled down by the blood-flow during the off-time. This is preferably harmonized with the heartbeat frequency. Optionally, the pulse-frequency can be triggered by the patient's actually measured heartbeat. The triggers are not impulse patterns, because a jump in power may cause pain or inconvenience in the patient. It is a modulation trigger with an amplitude modulation of 95% depth, and so the start and the end of a pulse feels smooth and is controlled. It can't start or end suddenly.

The heartbeat pulsation underlies a definite change during the heat exchange. This effect could be used for better drug-perfusion without increasing temperature. The "blood-flush" periodically cools unpleasant higher heating and so higher power can be applied without any safety risk or inconvenience of the patient. This triggering is harmonized with the patient's current heart rate. So if it is changing due to the decreasing or increasing temperature it is automatically corrected by the electronics. The heartbeat is monitored in situ at the place where the heating is generated with a conventional IR-sensor, so any delay or other time bias is avoided. If the objective is pumping high energy without overheating then the impulse will be opposite-in-phase, if the objective is a quick temperature increase then in-phase triggering has to be applied. For the embodiments disclosed herein being supportive for other therapies the opposite-in-phase triggering is preferred.

Arrhythmias or other heart problems must be handled of course very carefully as in any other electromagnetic treatment, irrespective of the triggering. In such a patient a continuous ECG is recommended, giving a warning signal at any irregular event. Optionally, the system includes a simple ECG monitor for safety reasons. However, if the tumor is sufficiently distant from the heart it is unlikely that any problem occurs, because the applied current is shortcut by the body tissue between the electrodes, and no effect should occur at a larger distance than the double perimeter of the electrode radius.

Moreover, persons having a pacemaker should not undergo any active electromagnetic treatment. Consequently, the present method applied by the inventive device is unsuitable for pacemaker patients irrespective of the selected modulation.

Another embodiment is that the power impulse regime is harmonized with the patient's heartbeat or is triggered by the patient's heart-beat (or heart-beat pulses). This enables even higher blood-perfusion rates in the targeted tissue and thus can further enhance the selective support of drug actions or can enhance the ionizing radiation.

The inventive portable RF hyperthermia device is especially useful for deep tissue heating by transporting energy to deep (1 mm to 10 mm) target tissue where the energy is converted to heat in the target tissue. The inventive device should not be confused with devices related to iontophoresis, electroporation and combination patches for local drug delivery. The present inventive device uses radiofrequency current-flow through the target which preferably is a human patient, but can also be any animal. In an embodiment the polarity of the current is rapidly changing by the periodic time of the frequency. In iontophoresis the polarity is unchanged (unidirectional arrangement), only the pulsing causes the effect, which is necessary because the applied voltage could cause serious damages and burns in the continuous mode. The applied DC current or rectified pulsed current has significant different effects than the RF device of the embodiments disclosed herein. All of these known devices treat the very surface area, keeping the energy at skin level, thus limiting their action on surface treatment. Electroporation is a high-voltage pulse treatment to make the cellular membrane more fluid, regulate their permeability or even building pores in the membrane, as well as to support the iontophoretic drug delivery with a powerful penetrating tool. Devices for such purposes do not disclose the use and are not able to use capacitive coupling and capacitive coupled electrodes as a capacitor in a high frequency circuit. The so-called capacitive coupling is applied in the DC-circuit, with the transient charge-redistribution effect as condenser characteristics. The complex impedance as a loading function of the AC/RF power supply (which is the main used feature in some embodiments) is not used in these known devices. The inventive portable RF hyperthermia device applies selectively through the tissue impedance a low electric field with high current and continuous AC or RF supply. The iontophoresis and electroporation apply a high electric field, low current and pulsing DC while such conditions can't be generated with some embodiments. Thus the inventive portable RF hyperthermia device does not use a high electric field, low current and does not use pulsing DC.

The parameters of the inventive portable radiofrequency (RF) hyperthermia device are strictly in the shape of a sinus wave, very "clean frequency", (not pulsing DC), applying the range of 0.1-15V/cm and preferable 0.5-5 V/cm (peak-to-peak). The RF-current is 0.5-5 A and preferable around 1 A. The frequency is in the range of 30 kHz to 70 MHz, preferable 13.56 MHz.

The portable radiofrequency (RF) hyperthermia device can be provided with preset and fixed frequency and power and is therefore simple to operate, thus being suitable for home use by a patient. Moreover, the portable RF hyperthermia device uses capacitive coupling and radio frequency waves and alternating current (AC) which makes modulation (triggering) possible which is optionally applied. These are completely different characteristics in comparison to what is used for iontophoresis or electromigration. Devices for iontophoretic effects work with unidirectional (DC) current. These devices cannot be operated with AC and/or RF.

The portable RF hyperthermia device is designed for a non-invasive hyperthermia treatment of the target tissue.

The portable RF hyperthermia device is especially useful for supporting any chemotherapeutical or radiotherapeutical treatment of tumors most preferably for the treatment of any tumors with low drug metabolism, low drug perfusion or low oxygenation.

The term "hyperthermia" as used herein refers to heating up a target higher than the environment equilibrium temperature.

The treated target tissue acts as a dielectric material of the capacitor in the electric field arrangement when the distance of the tissue from the portable RF hyperthermia device is less than the wavelength of the applied radio frequency (RF) wave, and the applied RF wave is tuned to fix the real-impedance value (preferably 50 Ohm).

The portable RF hyperthermia device can be a regarded as constraining RF-current through the body without radiative effect on the tissue.

The device also has a flexible applicator electrode, the flexible applicator is preferably in the form of a belt or bandage with preferably lightning fastener or any other fastener like Velcro®, buttons, buckles or straps. For example, it could be a belt-like shape having paired electrodes, for example with one pair or two pairs of capacitive electrodes as shown in FIG. 1.

These electrodes are an important part of the device. The belt electrodes or bandage electrodes are flexible, expandable, elastic and/or stretchable, can be provided in any desired size and can be easily used. The complete belt electrode or bandage electrode can form the conductive part of the electrode or only parts of the belt electrode or bandage electrode can form the conductive area of the electrode. These conductive parts or conductive areas can be made in any desired arrangement, shape, number and size. Preferably, also the conductive parts or conductive areas of the belt electrode or bandage electrode are flexible, expandable, elastic and/or stretchable so that they can adhere tightly to the area of the body which should be treated.

Figure 1:
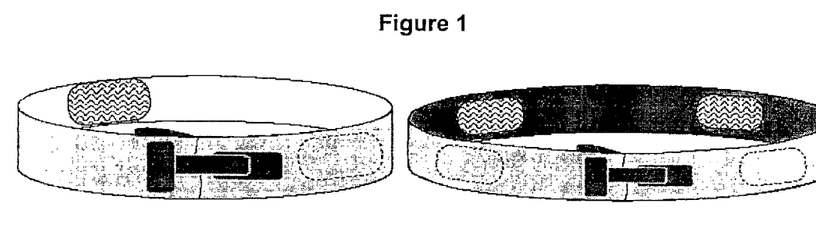
FIG. 1 shows an example of the belt-like shape electrode having one pair or two pairs of electrodes.

FIG. 1 shows a belt electrode or belt-like shape electrode. The areas within the dotted lines and the areas with wavy lines indicate the conductive part of the electrode while the left belt electrode has two and the right belt electrode has four conductive parts or electrodes. The conductive parts are preferably located opposite to each other and the two conductive areas which are located opposite to each other have preferably the same size.

Instead of a coated flexible, elastic or stretchable carrier or a coated flexible material a conductive metallic net or a conductive metallic network manufactured of at least one conductive metal electrode material can be used. Such metallic nets or metallic networks do preferably not comprise any backbone such as a polymeric network structure. The metallic net or network is preferably a woven structure of metallic fibres having very similar properties as the coated flexible material such a coated textile. The conductive metallic net or network is flexible, elastic or stretchable, allows water and other fluids as well as gases to move through it, can be folded without negative effect concerning conductivity and is able to cover uneven, fractal and/or percolative surfaces. Consequently, all kind of metallic nets and networks having the afore-mentioned properties of the conductively coated materials such as the conductively coated textiles are useful within the inventive electromagnetic energy transfer means.

Percolation is a phenomenon occurring when a volume of surface is filled up by linear connection possibilities which could find special linear connection pathways between the ends. For example, a typical percolative device is the well-known carbon-powder microphone the conduction of which was changed by the pressure on the membrane, because more percolative pathways in the powder were created by the pressure on the powder. The polymerization process shows also a percolation phenomenon, and presently the internet network can also be described with such a term. The coating of a textile (or any fibre-woven or non-woven sheets) definitely shows a percolation problem: The conduction path between the two electrodes could be various zig-zags in the sheet, and its conductivity depends on the number of the connection zig-zags (the degree of percolation).

The carrier or support or material and especially the solid carrier or solid support or solid material is made of plastic, polymers or natural substances such as biopolymers, is coated with a conductive material such as a conductive metal or metal alloy. Moreover, said coated carrier or coated support or coated material is porous and allows a liquid to pass through said carrier or support or material. Furthermore, the coated carrier or coated support or coated material is flexible, i.e. does not have a definite or predefined shape and is able to follow the uneven curvatures of the human or animal body or any cavity containing liquids, fluids, gas or solid substances which should be heated up.

The term "porous" as used herein refers to the ability that the coated carrier or coated support or coated material allows water and any gas to move through said coated carrier or coated support or coated material. The pore size can be up to 0.1 mm or even larger.

The inventive electrode comprises a flexible porous material, carrier or support coated with conductive metal so that the inventive energy transfer means acts like an radiative antenna or could be heated up alone by the current-flow through it. The inventive energy transfer means can be used for radiative microwave treatment, when radiative antennas (or magnetrons or other sources) pump the energy into the target, and it is also applicable in a phase-array arrangement, when the radiative antennas are placed around the target, and collectively controlled by their phase to make the best interference pattern in the desired volume. These radiative solutions, however, are not the basis of the present disclosure, which uses aforesaid electrodes. The advantages lie in the RF conductive regime, and not in radiation. In case of conduction the target is involved in the electric circuit like a part of it, while in the radiative case the target is out of the circuit, the energy is released from the electrons and absorbed independently by the target.

A porous textile is suitable as the flexible material or flexible, elastic or stretchable carrier or flexible, elastic or stretchable support. However any porous material having flexibility similar to the flexibility of a woven or non-woven textile could also be used. Thus any kind of textile, woven textile, non-woven textile and even non-textile material is suitable as flexible porous material. Such a flexible porous material can also be named as a flexible porous solid support or flexible porous solid carrier. Such materials, carrier or supports are not limited by a specific shape and have the consistency and/or texture of a piece of textile or a piece of fabric or drapery. Consequently, all known natural and artificial materials such as polyamide (Nylon®), poly-ε-caprolactone, poly-para-dioxanones, polyanhydrides, polyhydroxymethacrylates, fibrin, polyetherester, PEG, poly(butylene terephthalates), polycarbonates, poly(N-vinyl)-pyrrolidone, polyvinylalcohols, polyesteramides, polyethyleneoxide, polypropyleneoxide, polyurethanes, fibrinogen, starch, collagen, zein, casein, β-cyclodextrins, polyacrylates, polyacrylamide, polyimides, polyethylene, polypropylene, polytetrafluoroethylene, fluorosilicones, rayon, polysulphones, silicones, polysiloxanes, polyvinyl halogens and copolymers or mixtures of these substances can be used.

Preferred are materials, carrier or supports such as these mentioned before which provide a good adhesion for the metallic coating. Also preferred are materials, carrier or supports which are manufactured of or which consist of a plurality of single fibres like a woven textile wherein one set of the single fibres extends along the complete length of the textile more or less in a substantially parallel manner while the other set of fibres is arranged in a substantially parallel manner diagonal to the first set of fibres. Thus fibres having a length which is similar to the length of the textile comprising said fibres are preferred.

In a further preferred embodiment the single fibres of the material, carrier or support are coated like a tube which means not only a part of the surface of the fibre is coated rather the coating is applied all around the fibre.

Moreover it is preferred that such material, carrier or support is percolative and/or fractal or has a percolative and/or fractal structure without any discontinuity between the in and out cables of the electromagnetic energy transfer means. In other words, the metallic nets or the coated carriers are such flexible that they are able to cover uneven, fractal or percolative surfaces or they are able to follow the structure of uneven, fractal or percolative surfaces.

The conductive metal coating is a multilayer coating. Preferably, one of the layers is silver which has a good antibacterial effect and provides for good radiofrequency (RF) conduction. Moreover, silver has an anti-odour effect together with moderate anti-perspiration activity. This makes silver preferred for cosmetic, medical and well-being applications.

However, other conductive metal coatings can also be used. The resulting conductive metal coated flexible material is still sufficiently porous to allow for the exchange of heat and fluids. Preferably the electroless (autocatalytic) deposition of the conductive metal coating is used which is one of the most frequently used methods for fabricating coatings for corrosion- and wear-resistant purposes. The term "electroless coating" or "electroless deposition" refers to the building of a metallic coating from an electrolyte by way of immersion. Metallization of any non-conductive materials (e.g. plastics) occurs always (at least at the beginning) in such a chemical process. It is autocatalytic, using platinum or palladium salts to fix the first clusters on the surface "dangling" bonds.

The textile can be coated by extra plastic layer for galvanic isolation. This should preferably not be a continuous layer, but a layer on the fibres only in order to keep the porous structure free and open. If the device is double isolated, direct metallic contact could be used. The multilayer structure coats the fibres co-axially and perfectly continuous. If the metal layer-making technology is dipping electroless process then the crossing of individual fibres could be also perfectly coated individually fibre by fibre, if it is galvanic, then the crossings could be coated only as a cross, not keeping the individual fibre co-axial structure. The plastic coating, however, has to be dipping with such surface tension of the bath, which does not allow the isolation of the metallic coated fibres at their crossing, only coats their outer surface, however the coating does not fill up the pores, so the material remains porous.

Ideally, treatment electrodes or applicators are used that are suitable for application to all parts of the human body. For this reason there is a need for a flexible electrode/applicator that can conform to the contours of the body. The coated flexible carrier or the flexible metallic net acts as an electrode for the treatment of a large and/or uneven, fractal and/or percolative surface while these carriers or metallic nets can easily be fixed on said surface via a belt or bandage, or the like.

The inventive flexible electric field capacitive coupled electrode is able to fulfil this requirement, i.e. to be conductive, flexible, foldable, porous and able to cover uneven, fractal and/or percolative surfaces smoothly like a cloth following the contour of the surface. The flexible electrode applicator is formed from a conductive metal coated flexible material or a metallic network that can be folded or formed freely even into a cylinder-like shape. Thus the inventive electrode can conform to gradual and sharp curvatures. For example, in the case of sharp curvatures it can easily conform to the shape of a limb by wrapping around the limb or can conform to the shape of the skull. Alternatively, in the case of gradual curvatures it can conform to the shape of the torso.

Also the inventive flexible electromagnetically coupled electrode applicator is lightweight and therefore can be produced to cover a large area, such as the torso, without causing discomfort to the patient due to excessive weight of the electrode applicator. This allows for the treatment of large areas in a single treatment session. Also the flexibility of the energy transfer means allows for a good contact between the applicator and a large application area, for example, the torso.

The inventive flexible electromagnetically coupled electrode applicator is also porous. This allows for natural cooling of the treatment area due to exchange of heat through the energy transfer means via convection. Also a simple external air cooling system, for example a directed air flow from a fan, can be used to cool the application area to prevent burning and maintain patient comfort. As a result there is no requirement for a complicated fluid cooling system as is the case in conventional bolus electrodes. This allows for a simple and lightweight construction that is suitable for home use by a patient.

Additionally, an extra air or fluid cooling can optionally be introduced to the electrodes. An air-cooling by conventional ventilation from a definite distance could be applied. The fluid cooling is another optional solution, but the simplest is a wet textile tissue covering the electrodes. The fluid itself and the evaporation of the fluid cause intensive cooling. This can be combined with air-cooling to generate more intensive evaporation, using the necessary latent heat.

Thus the inventive portable RF hyperthermia device may comprise a part or device to wet, moisten and/or temper the electrodes and preferably to continuously wet, moisten and/or temper the electrodes. For the wetting or moistening preferably water is used. Instead of or in addition to the wetting or moistening device an air-cooling device can be part of the inventive hyperthermia device which is used for cooling purposes. Especially preferred is the combination of the wetting or moistening device together with an air-cooling device, since the additional air-cooling increases evaporation of the cooling fluid (such as water) so that an additional cooling effect is achieved.

The porosity of the electrode applicator also allows for the exchange of fluids through the electrode applicator. Thus perspiration can evaporate naturally through the porous electrode applicator and therefore increase the patient's comfort.

Additionally, extra temperature measurement could be done on the surface of the electrodes. This is only for safety reasons, because the adipose tissue (fat) could cause a too high drop of the voltage possibly causing a burn of the surface. To avoid such a complication the surface temperature can be measured. The temperature measurement is only a safety issue and not part of the treatment.

In a preferred embodiment, the portable RF hyperthermia device contains or includes means for temperature measurement. Said means for temperature measurement could be thermometers which are able to accurately measure the temperature, preferably measure the temperature in average over a large area which covers preferably at least the treated area. The temperature measurement has to be "RF-tolerable" in a wide range of frequency (up to 15 MHz), so its measured value must not be modified by the active field or its fluctuations. The means for temperature measurement could be a thermo-pair or thermistor or platinum-resistor or other temperature sensing structure/element. Preferable are micro-thermistors.

The measured temperature is preferably filtered with high level filters. Their role is to avoid incorrect thermo-signals caused by RF-field or by its induced currents, which could bias the measured signal. This filter is preferably a resonant serial circuit, (or in a simple case could be a condenser only, having low admittance in the given frequency) tuned to the applied frequency. Its resonance/conduction shortcuts the actual RF, but does not modify the measuring signal of the thermo-element. This solution keeps the thermo-signal correct and intact from the RF-effects. The filter is preferably built in directly at each sensor (preferably smallest SMD parts 0.2 mm in size).

Moreover, it is preferred that the inventive portable RF hyperthermia device comprises a temperature sensing electric system. The temperature sensing electric system is preferably highly isolated from the ground (at least 4 kV) for safety reasons. The thermistor resistivity is not measured by DC, which could be sensitive for RF-noises. The thermo-signal is measured with a low frequency RF, far from the treatment frequency, (preferably 80 kHz at 339 kHz carrier and in audio-range modulation range) but outputting a sufficient signal amplitude for the preferable isolating transformer or opto-connection transmission to isolate on 4 kV standard value.

It is preferred that the temperature is measured in the center and at the border of the RF electrode, measuring the average temperature of the treated surface in the middle and at the boarder of the treated area. The applied thermo-sensor has to be as near as or as close as possible to the surface and to the treated tissue. For the perfect thermal sensing the sensors are in direct tight contact with the RF electrode.

Due to the simple construction of the inventive flexible electrode applicator it can be provided as a single use disposable electrode or could be produced to specification for an individual patient. A further advantage of the inventive flexible electrode applicator is that there is no requirement for a bulky, rigid-frame and difficult to operate bolus electrode applicator. Thus it is suitable for home use by a patient.

Thus the embodiments disclosed herein relate to a portable radiofrequency (RF) hyperthermia device having flexible applicator treatment electrodes for electric field capacitive coupled energy transfer, the device being useful for increasing the delivery of a systemically delivered drug at a localised target site. The portable RF device is suitable for use by a patient in their own home and the flexible applicator is a flexible, porous, light and easy to manipulate treatment electrode. The inventive device requires no specialist operator to ensure correct usage.

Preferably the localised target site is selected from tumor tissue and muscle tissue, or organs, such as for example, liver, lung, heart, kidney, spleen, brain, ovary, uterus, prostate, pancreas, larynx, the gastrointestinal tract and the gynaecological tract.

Preferably the flexible applicator treatment electrodes comprise at least one conductive metal electrode material in form of a coating or a metallic net, wherein at least one conductive metal electrode material layer is coated onto the surface of a flexible carrier, and wherein the coated flexible carrier is porous. Instead of the coated flexible material a metallic net or a network of metallic fibres can be used.

Preferably the conductive metal electrode material is selected from silver, nickel, copper, gold and alloys containing silver, nickel, copper and/or gold.

The flexible material is usually polypropylene or polyamide. Polyurethane or other plastics as well as the above mentioned materials are also suitable. The flexible material has a woven or non-woven structure. Textiles made from natural fibres (cotton, wool etc.) have normally too short fibres with rough surfaces, so their specific surface is too large to coat it effectively with something.

The coated surface or the coated sheet of flexible material allows the movement of air and water/aqueous solution through the material. The coated sheet of flexible material allows the movement of fluid through the material.

The coated sheet of flexible material can form a cylinder. The coated sheet of flexible material can also be folded.

The size of the electrode is not limited, but of course is adjusted to the application of interest, i.e. for instance to the body part that should be treated by hyperthermia treatment.

Preferably, the radiofrequency of the portable radiofrequency device is fixed.

Preferably, the energy transfer is delivered via a power impulse regime and further preferably the power impulse regime is harmonized with the patient's heartbeat.

Another embodiment is the use of the portable radiofrequency (RF) hyperthermia device having flexible applicator treatment electrodes for electric field capacitive coupled energy transfer to provide an improved method for increasing the delivery of a systemically delivered drug at a localised target site. The at least 2 flexible applicator treatment electrodes are incorporated in at least one flexible, expandable, elastic and/or stretchable belt or bandage. This belt or bandage with the at least two electrodes is referred to herein as bandage electrode, belt electrode or belt-like shape electrode.

Thus, the hyperthermia device can be used to increase the delivery of a systemically delivered drug at a local target site wherein the local target site is selected from tumor tissues and muscle tissue, or organs, such as for example, liver, lung, heart, kidney, spleen, brain, ovary, uterus, prostate, pancreas, larynx, the gastrointestinal tract, and the gynaecological tract.

The tumor tissue can be selected from adenocarcinoma, choroidal melanoma, acute leukemia, acoustic neurinoma, ampullary carcinoma, anal carcinoma, astrocytoma, basal cell carcinoma, pancreatic cancer, desmoid tumor, bladder cancer, bronchial carcinoma, non-small cell lung cancer (NSCLC), breast cancer, Burkitt's lymphoma, corpus cancer, CUP-syndrome (carcinoma of unknown primary), colorectal cancer, small intestine cancer, small intestinal tumors, ovarian cancer, endometrial carcinoma, ependymoma, epithelial cancer types, Ewing's tumors, gastrointestinal tumors, gastric cancer, gallbladder cancer, gall bladder carcinomas, uterine cancer, cervical cancer, cervix, glioblastomas, gynecologic tumors, ear, nose and throat tumors, hematologic neoplasias, hairy cell leukemia, urethral cancer, skin cancer, skin testis cancer, brain tumors (gliomas), brain metastases, testicle cancer, hypophysis tumor, carcinoids, Kaposi's sarcoma, laryngeal cancer, germ cell tumor, bone cancer, colorectal carcinoma, head and neck tumors (tumors of the ear, nose and throat area), colon carcinoma, craniopharyngiomas, oral cancer (cancer in the mouth area and on lips), cancer of the central nervous system, liver cancer, liver metastases, leukemia, eyelid tumor, lung cancer, lymph node cancer (Hodgkin's/Non-Hodgkin's), lymphomas, stomach cancer, malignant melanoma, malignant neoplasia, malignant tumors gastrointestinal tract, breast carcinoma, rectal cancer, medulloblastomas, melanoma, meningiomas, Hodgkin's disease, mycosis fungoides, nasal cancer, neurinoma, neuroblastoma, kidney cancer, renal cell carcinomas, non-Hodgkin's lymphomas, oligodendroglioma, esophageal carcinoma, osteolytic carcinomas and osteoplastic carcinomas, osteosarcomas, ovarial carcinoma, pancreatic carcinoma, penile cancer, plasmocytoma, squamous cell carcinoma of the head and neck (SCCHN), prostate cancer, pharyngeal cancer, rectal carcinoma, retinoblastoma, vaginal cancer, thyroid carcinoma, Schneeberger disease, esophageal cancer, spinalioms, T-cell lymphoma (mycosis fungoides), thymoma, tube carcinoma, eye tumors, urethral cancer, urologic tumors, urothelial carcinoma, vulva cancer, wart appearance, soft tissue tumors, soft tissue sarcoma, Wilm's tumor, cervical carcinoma and tongue cancer. Particularly suitable for treatment are, for example, astrocytomas, glioblastomas, pancreatic cancer, bronchial cancer, breast cancer, colorectal cancer, ovarian cancer, gastric cancer, laryngeal cancer, malignant melanoma, oesophageal cancer, cervical cancer, liver cancer, bladder cancer, and renal cell cancer Therefore, the hyperthermia device can be used in combination with chemotherapy treatment with cytostatic and/or cytotoxic drugs. Example of some cytostatic and/or cytotoxic drugs are actinomycin D, aminoglutethimide, amsacrine, anastrozol, antagonists of purine and pyrimidine bases, anthracycline, aromatase inhibitors, asparaginase, antiestrogenes, bexarotene, bleomycin, buselerin, busulfan, camptothecin derivates, capecitabine, carboplatin, carmustine, chlorambucil, cisplatin, cladribine, cyclophosphamide, cytarabine, cytosinarabinoside, alkylating cytostatics, dacarbacin, dactinomycin, daunorubicin, docetaxel, doxorubicin (adriamycin), doxorubicin lipo, epirubicin, estramustine, etoposide, exemestane, fludarabin, fluorouracil, folic acid antagonists, formestane, gemcitabine, glucocorticoides, goserelin, hormones and hormone antagonists, hycamtin, hydroxy urea, idarubicin, ifosfamide, imatinib, irinotecan, letrozole, leuprorelin, lomustine, melphalan, mercaptopurine, methotrexate, miltefosine, mitomycin, mitosis inhibitors, mitoxantrone, nimustine, oxaliplatin, paclitaxel, pentostatin, procarbazine, tamoxifen, temozolomide, teniposide, testolactone, thiotepa, thioguanine, topoisomerase inhibitors, topotecan, treosulfan, tretinoin, triptorelin, trofosfamide, vinblastine, vincristine, vindesine, vinorelbine, antibiotics with cytotoxic activities. All the present and future cytostatics or other medicaments including gene therapy could be applied.

When used for treatment of inflammatory conditions the hyperthermia device can be used in combination with an anti-inflammatory drug treatment such as a non-steroidal anti-inflammatory drug (NSAID), for example, alclofenac, aceclofenac, sulindac, tolmetin, etodolac, fenopren, tiaprofenic acid, meclofenamic acid, meloxicam, tenoxicam, lornoxicam, nabumetone, acetaminophen, phenacetin, ethenzamide, sulpyrine, mefanamic acid, flufenamic acid, diclofenac sodium, loxoprofen sodium, phenylbutazone, indomethacin, ibuprofen, ketoprofen, naproxen, oxaprozin, flurbiprofen, fenbufen, pranoprofen, floctafenine, piroxicam, epirizole, tiaramide hydrochloride, zaltoprofen, gabexate mesilate, camostat mesilate, ulinastatin, colchicine, probenecid, sulfinpyrazone, benzbromarone, allopurinol, salicylic acid, atropine, scopolamine, levorphanol, ketorolac, tebufelone, tenidap, clofezone, oxyphenbutazone, prexazone, apazone, benzydamine, bucolome, cinchophen, clonixin, ditrazol, epirizole, fenoprofen, floctafenine, glaphenine, indoprofen, niflumic acid and suprofen, or with a steroidal anti-inflammatory drugs, for example, dexamethasone, hexestrol, methimazole, betamethasone, triamcinolone, fluocinonide, prednisolone, methylprednisolone, hydrocortisone, fluorometholone, beclomethasone dipropionate, estriol, clobetasol, diflorasone diacetate, halobetasol propionate, amcinonide, desoximetasone, halcinonide, mometasone furoate, fluticasone propionate, flurandrenolide, clocortolone, prednicarbate, alclometasone dipropionate and desonide.

The portable radiofrequency hyperthermia device having flexible applicator treatment electrode for electric field capacitive coupled energy transfer, the device being useful for increasing the delivery of a systemically delivered drug at a local target site and method provides the following significant advantages over prior art devices and methods.

The main advantage of the portable RF hyperthermia device is the deep heating of the tissue (deep heat delivery). Deep heating of the target tissue means delivery of energy and generation of heat in a depth of 1 mm to 10 mm which is very effective for cancer treatment especially for the treatment of epithelial cancer and other skin cancers. Moreover, the inventive device is able to enhance the capillary blood-flow and can be applied locally with a focused effect. This leads to better and targeted drug delivery as well as to better and targeted oxygen delivery (higher drug metabolism and higher ionization efficacy for radiotherapies) and enables the penetration of pharmaceutically active agents through the blood-brain-barrier.

Deep Heat Delivery

The heat delivery can not be made for deep-targeting purposes by conventional heat-diffusion (from the heated surface-skin) alone. The skin heating makes higher blood-perfusion in the capillary-bed of the skin, and this effectively shields deeper penetration. This is one of the physiologic defence mechanisms of highly organized organisms for keeping the body temperature independent of the wide range of ambient temperatures. The deep heat is created by the effective electric current flow (and its absorbed Joule-heat) across the targeted volume. The heat generated by the portable RF hyperthermia device is directly induced in the target; consequently it is localized enough for local consequences without heating large areas outside the target. This deep heat-penetration is missing in all known hyperthermia devices of the state of the art such as the devices disclosed in U.S. Pat. No. 6,330,479 B1 and WO 00/51513 A.

Enhancing Capillary Blood-Flow

The local temperature higher than its surrounding physiologically promotes blood-perfusion. Consequently, the locally enhanced blood perfusion in deep volume will deliver more drug and more oxygen than to the surrounding, a key factor for the efficacy of pharmaceutical and of radio-ionization actions, respectively. The heat-diffusion solutions (surface heating) are increasing mostly the drug perfusion on the surface area and not (or at least considerable less) in the desired target area. This is again an important differentiation form the state of the art embodiments as mentioned in U.S. Pat. No. 6,330,479 B1 and WO 00/51513 A.

It is important to notice that the current density in the targeted volume has a positive feedback for inducing blood-perfusion. The enhanced blood perfusion leads to higher conductivity, which concentrates more the current density on the volume (having a higher conductance than before), which heats more the actual target, which promotes the higher blood-perfusion and so on.

Local and Focused Effect

The deep heat delivery is not only a booster of blood perfusion, but also promotes local chemical reactions (by the well-known exponential Arrhenius law), and so enhances locally the chemo-metabolism and the desired effects in the locally heated area. It is important that this higher metabolism generates again a positive feedback, because it is accompanied by a higher ionic exchange between the electrolytes in the living system, so produces more ionic species in the volume, and again increases its conductivity, attracting more currents, and the higher current density enhances the full process in a positive loop. The higher temperature promotes the metabolic processes, which are ionic exchanges between the electrolytes through the membrane surface. The intensive metabolic activity without adequate oxygen supply produces lactic acid, which commonly occurs through excessive muscle activity (muscular-strain, fatigue-fever).

Furthermore, the brain has a specific physiological defence mechanism, the blood-brain-barrier (BBB). Its penetration by certain drugs is one of the most complicated tasks of CNS medication. The RF-current definitely lowers the BBB protection, enabling a higher drug penetration into the desired brain areas.

The flexible applicator treatment electrode is simple to use and requires no specialist operator to ensure correct usage. Also the device provides the significant advantage that delivery of a systemically delivered drug to a localised target site can be increased during home treatment with the systemically delivered drug and no hospital admission or clinic visit is required to make use of the device. The fixed radiofrequency inventive device requires no specialist operator to ensure correct usage. Further, the power impulse regime, preferably harmonised to the heartbeat, allows the blood flow to cool the surface area during the pulse off-time.

Figure 5:
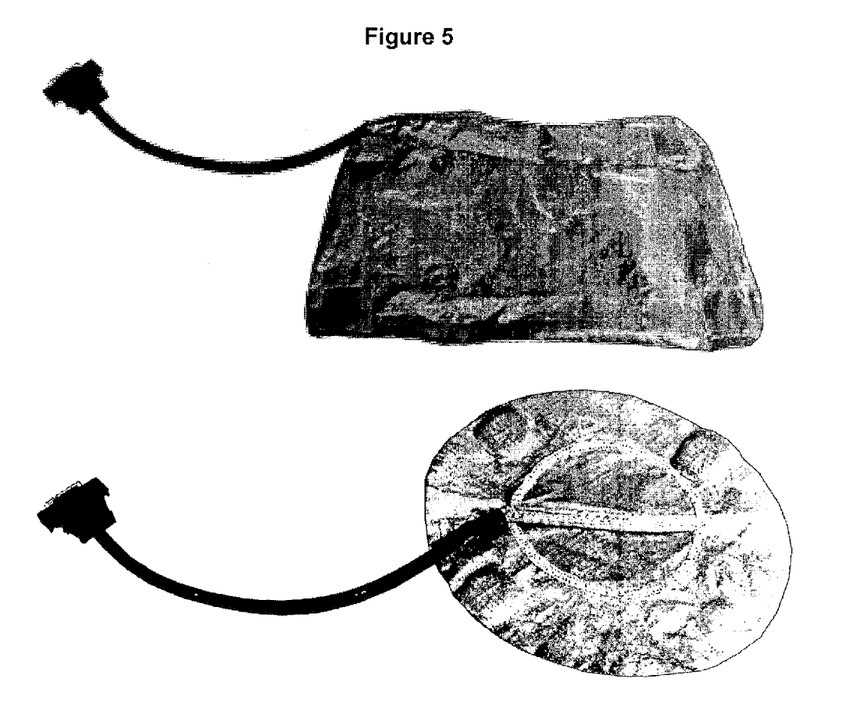
FIG. 5 shows two embodiments of flexible applicator treatment electrodes. The first embodiment is a rectangular electrode and the second embodiment is a round flexible applicator treatment electrode. Also the single connection cable with the plug at the end is depicted. Moreover, it is evident from FIG. 5 that the flexible applicator treatment electrodes are light, highly flexible, easy to use, comfortable for the patient and require only a single cable for the connection to the hyperthermia device.

The electric contacts are pure metallic wires sewn up into the flexible electrode, like a boarder (frame) made by inseam around the electrode. Any of the size and form is possible, could be done by confection like a T-shirt, bra, panty, etc. The power supply is directly connected to the wire sewn up in the electrode (see FIG. 5).

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

SCID mice with a human medulloblastoma tumor were treated using the claimed device and electrode.

Three animals were inoculated symmetrically with two tumors in their femoral region. One of the tumors was treated, the other was used as individual control. The tumor was measured by SPECT-CT (MEDISO product) and the treatment was single shut, 30 min, 15 W. The treatment was made by LabEHY100 (a product of the applicant), 13.56 MHz, no pulsative modulation was applied.

This example demonstrates the effect of the embodiments disclosed herein: The blood-perfusion is higher in the treated tumor than in its control counterpart. This effect supports any chemo- or radiotherapy.

It is not a treatment for tumor healing, it is a booster for other oncotherapies to heal. What this example demonstrates is not the treatment of the tumor itself by hyperthermia, but the blood-flow increase, which is simply shown.

Location of the tumor: femoral region.

Radiopharmaceutical: $^{99m}$Tc labelled liposome was applied. (Injected dose: 35 MB q/0.1 mL)

The result was measured by high-tech SPECT (Single Photon Emission Computed Tomography).

Figure 2:
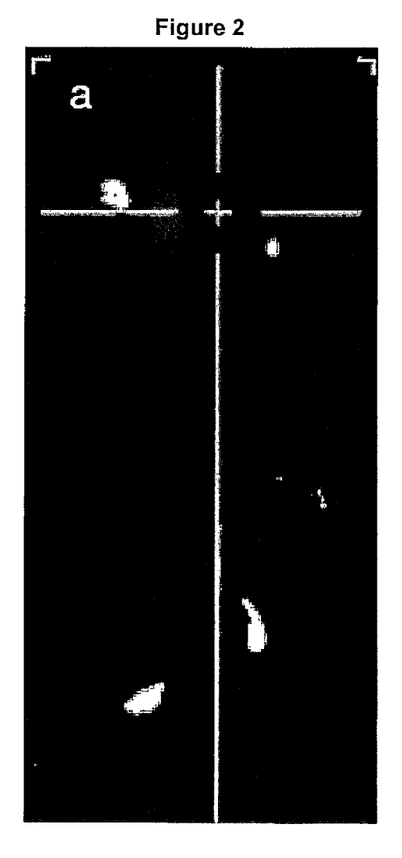
FIG. 2 shows the measurement of the mouse tumor with symmetrical control. (a) the result in depth.

Results clearly demonstrate the enrichment of the labeled drug in the treated region (FIG. 2). One can see a higher intensity of the labelled drug in the boosted region, so the blood-perfusion was higher there which is the aim of the treatment.

Example 2

HT29 tumor bearing nude mice were treated using the claimed device and electrode and the distribution changes of cholesterol enriched phospholipid liposomes labelled with $^{99m}$Tc were investigated.

If nothing else is stated, the same conditions as in example 1 were used.

Location of the tumor: femoral region

Radiopharmaceutical: Cholesterol enriched phospholipid liposomes labelled with $^{99m}$TC (injected dose: 60 MBq/0.15 mL iv.)

The result was measured by high-tech SPECT (Single Photon Emission Computed Tomography).

Figure 3:
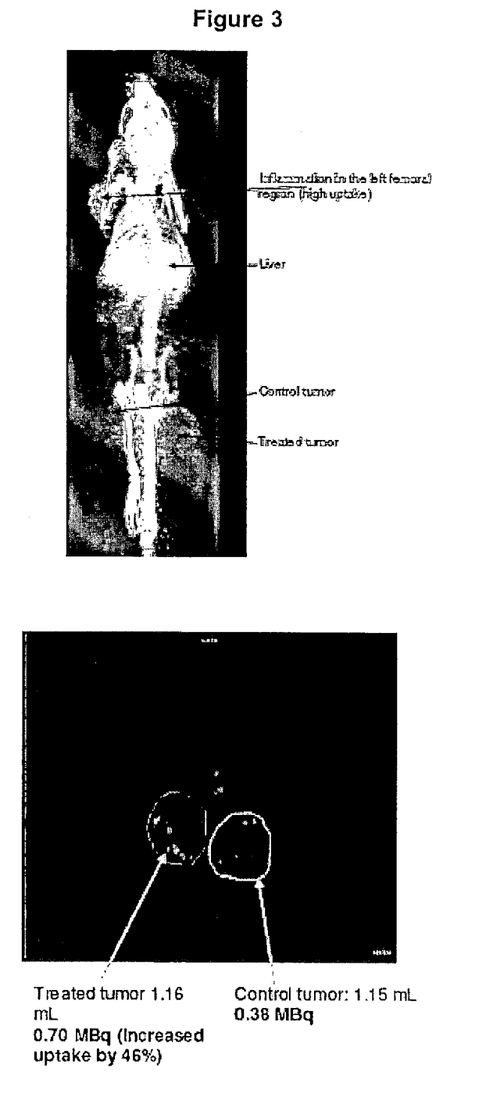
FIG. 3 shows the SPECT pattern and its evaluation.

The gain of the enrichment of the radiopharmacon due to the increased blood-perfusion was 46% in comparison to the control (FIG. 3). Also the drug enrichment in the area is experimentally proven.

Example 3

The same blood-perfusion increase was seen in a healthy beagle dog in comparison of the two femoral regions.

If nothing else is stated, the same conditions as in example 1 were used.

Radiopharmaceutical (400 MBq 99 mTc-HAS) by injection. The measurement was performed by SPECT (Single Photon Emission Computed Tomography). Boosting treatment is a single shot, 30 min, 30 W. The blood perfusion in the treated tissue of a healthy beagle dog was measured after treatment with the claimed device and electrode and is definitely higher than in the untreated control.

Figure 4:
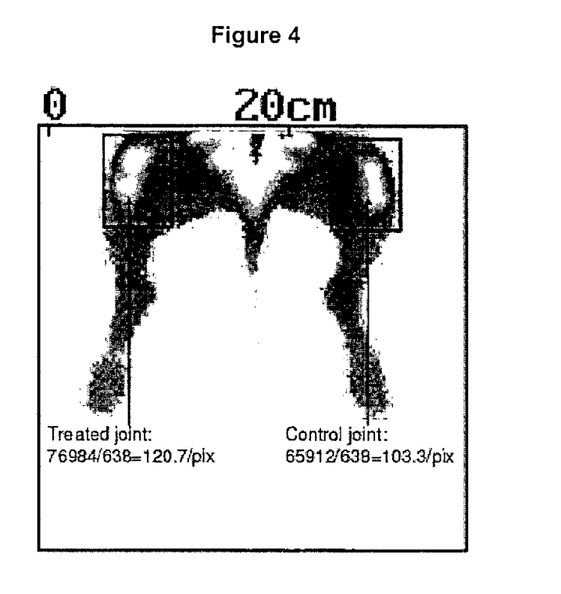
FIG. 4 shows the enrichment of a radiopharmacon which shows increased blood flow.

The result shows a blood flow enhancement of 16.8% in the treated joint (FIG. 4).

The invention claimed is:

1. A portable radiofrequency hyperthermia device configured for cancer treatment comprising a flexible applicator treatment electrode for electric field capacitive coupled energy transfer to create an RF current flow through a patient without a fluid cooling system and a radiofrequency amplifier, the device being useful for increasing the delivery of a systemically delivered drug at a local target site, and/or supporting the radiotherapy efficacy in the localized target site by increasing the oxygenization of the tissue and capable of home use by the patient;
   wherein the radiofrequency amplifier is an E-class radiofrequency amplifier;
   wherein the flexible applicator treatment electrodes comprise at least one conductive metal electrode material in form of a coating on the surface of a flexible, elastic, or stretchable carrier,
   wherein the coating is an electroless deposition coating, and wherein the coated flexible, elastic or stretchable carrier is porous and wherein the carrier comprises a plurality of single fibers and the at least one conductive metal electrode material layer is applied all around the single fibers of the carrier; and
   wherein the local target site is selected from tumor tissue, muscle tissue, or organs, the organs is selected from the group consisting of liver, lung, heart, kidney, spleen, brain, ovary, uterus, prostate, pancreas, larynx, gastrointestinal tract and gynecological tract; and
   wherein the energy transfer is delivered via a power impulse regime and the power impulse regime is harmonized with a patient heartbeat or is triggered in an amplitude modulated way with patient heart-beat pulses, measured at the site of treatment.

2. The portable radiofrequency device of claim 1, wherein the conductive metal electrode material is selected from silver, nickel, copper, gold and alloys containing silver, nickel, copper and/or gold.

3. The portable radiofrequency device of claim 1, wherein the flexible carrier is selected from a textile, a plastic, polyamide, poly-ε-caprolactone, poly-para-dioxanones, polyanhydrides, polyhydroxymethacrylates, fibrin, polyetherester, PEG, poly(butylene terephthalates), polycarbonates, poly(N-vinyl)-pyrrolidone, polyvinylalcohols, polyesteramides, polyethyleneoxide, polypropyleneoxide, polyurethanes, fibrinogen, starch, collagen, zein, casein, β-cyclodextrins, polyacrylates, polyacrylamide, polyimides, polyethylene, polypropylene, polytetrafluoroethylene, fluorosilicones, rayon, polysulphones, silicones, polysiloxanes, polyvinyl halogens and copolymers or mixtures of these substances.

4. The portable radiofrequency device of claim 1, wherein the coated flexible, elastic or stretchable carrier allows the movement of air through the carrier.

5. The portable radiofrequency device of claim 1, wherein the coated flexible, elastic or stretchable carrier allows the movement of fluid through the carrier.

6. The portable radiofrequency device of claim 1, wherein the coated flexible, elastic or stretchable carrier can form a cylinder or any other form adapted to any shape of a human or animal body.

7. The portable radiofrequency device of claim 1, wherein the coated flexible, elastic or stretchable carrier net can be folded.

8. The portable radiofrequency device of claim 1, wherein the radiofrequency is fixed.

* * * * *